(12) United States Patent
Maurello

(10) Patent No.: US 9,242,164 B2
(45) Date of Patent: Jan. 26, 2016

(54) MOUTHGUARD ASSEMBLY

(71) Applicant: John Maurello, Oceanside, NY (US)

(72) Inventor: John Maurello, Oceanside, NY (US)

(*) Notice: Subject to any disclaimer, the term of this patent is extended or adjusted under 35 U.S.C. 154(b) by 336 days.

(21) Appl. No.: 13/740,540

(22) Filed: Jan. 14, 2013

(65) Prior Publication Data

US 2014/0196725 A1  Jul. 17, 2014

(51) Int. Cl.
| | |
|---|---|
| A42B 1/06 | (2006.01) |
| A42B 7/00 | (2006.01) |
| A42B 1/24 | (2006.01) |
| A42B 1/08 | (2006.01) |
| A63B 71/10 | (2006.01) |
| A61F 5/37 | (2006.01) |
| A61F 5/56 | (2006.01) |
| A61F 11/00 | (2006.01) |
| A61C 5/14 | (2006.01) |
| A61C 3/00 | (2006.01) |
| A61C 19/00 | (2006.01) |
| A61C 9/00 | (2006.01) |
| A63B 71/08 | (2006.01) |
| A61C 7/08 | (2006.01) |
| A61F 5/00 | (2006.01) |
| A63B 49/00 | (2015.01) |
| A61C 1/00 | (2006.01) |
| A61C 7/00 | (2006.01) |

(52) U.S. Cl.
CPC ............. *A63B 71/085* (2013.01); *A61C 1/00* (2013.01); *A61C 7/00* (2013.01); *A61C 7/08* (2013.01); *A61F 5/00* (2013.01); *A61F 5/56* (2013.01); *A61F 5/566* (2013.01); *A63B 49/00* (2013.01); *A63B 71/08* (2013.01); *A61C 9/00* (2013.01); *A61C 9/002* (2013.01); *A63B 2071/088* (2013.01); *A63B 2210/50* (2013.01)

(58) Field of Classification Search
CPC ........ A63B 49/00; A63B 71/00; A63B 71/08; A63B 71/085; A63B 71/088; A61C 1/00; A61C 7/00; A61C 7/08; A61C 9/00; A61C 9/002; A61F 5/00; A61F 5/56; A61F 5/566
USPC .............. 2/410, 421–422, 424–425; 128/846, 128/848, 857, 859, 861–862; 433/6, 7, 34, 433/37, 41, 43, 53
See application file for complete search history.

(56) References Cited

U.S. PATENT DOCUMENTS

| | | | | |
|---|---|---|---|---|
| 5,018,967 | A * | 5/1991 | Schwalbach | A61C 19/063 433/215 |
| 5,409,017 | A * | 4/1995 | Lowe | A61C 7/10 128/848 |
| 5,820,372 | A * | 10/1998 | Jones | A61C 9/0006 433/38 |
| 6,082,363 | A * | 7/2000 | Washburn | 128/859 |
| 7,353,828 | B1 * | 4/2008 | Hirshberg | A63B 71/085 128/859 |
| 7,708,018 | B1 * | 5/2010 | Hirshberg | 128/861 |
| 7,913,695 | B1 * | 3/2011 | Moore | A63B 71/085 128/861 |

(Continued)

Primary Examiner — Alireza Nia
Assistant Examiner — Brandon L Jackson
(74) Attorney, Agent, or Firm — Dan De La Rosa

(57) ABSTRACT

A mouthguard assembly is provided. The mouthguard assembly includes a generally curved mouthguard for insertion into a user's mouth having an outer portion and inner portion, a channel formed within the outer or inner portion of the mouthguard, and an attachment means housed within the channel. The user can extend the attachment means out of the channel to temporarily attach the mouthguard assembly to clothing or apparatus of the user for storage of the mouthguard when it is not used.

19 Claims, 2 Drawing Sheets

(56) References Cited

U.S. PATENT DOCUMENTS

| | | | |
|---|---|---|---|
| 8,018,967 B2 * | 9/2011 | Kameyama et al. | H04N 21/2383 370/474 |
| 8,074,658 B2 * | 12/2011 | Kittelsen et al. | 128/861 |
| 8,603,393 B1 * | 12/2013 | DolceAmore | 422/28 |
| 8,635,731 B2 * | 1/2014 | Garner et al. | A46B 9/045 15/22.1 |
| 2007/0151568 A1 * | 7/2007 | Maurello | 128/859 |
| 2012/0012120 A1 * | 1/2012 | Giffey et al. | 128/860 |
| 2014/0350354 A1 * | 11/2014 | Stenzler | A61B 5/4818 600/301 |

* cited by examiner

MOUTHGUARD ASSEMBLY

BACKGROUND

The present invention relates to a mouthguard for use in athletics and more particularly, to a mouthguard that can temporarily be stored by a user on their clothes or apparatus.

Mouthguards have been developed and sold for several years for protecting the mouth and teeth of an athlete from injuries that may result from impact collisions and blows during athletic competition. Mouthguards have been used in several contact sports including football, basketball, ice hockey, soccer and lacrosse where collisions between players are common. Mouthguards generally consist of a somewhat U-shaped device that fits around the upper and lower teeth of the user and are historically categorized as custom fit or non-custom fit. Custom fit mouthguards generally provide better protection for athletes, but are expensive and require a dentist for proper fabrication and fitting. Non-custom fit mouthguards are designed to fit generally for most users and are commonly used, however, these mouthguards are often inadequate for various reasons such as improper fit, uncomfortable teeth and jaw positioning, and a lack of temporary storability which can lead to a risk of infection. In particular, athletes typically remove mouthguards during breaks in athletic competition and carry their mouthguard in their hands and then reinsert it into their mouth immediately before athletic competition resumes. Holding a mouthguard in the user's hand can lead to germs coming into contact with the mouthguard before it is placed back into the user's mouth.

To address concerns such as storability and essentially the risk of infection, various mouthguards have been designed with a strap or a tether attached to the front of the mouth guard on a tab. For example, in football, mouthguards with straps connected to the face mask of a football helmet have been designed and utilized. Such a design eliminates the problem of having to carry a mouthguard in the user's hand or squeezing it into a portion of a football helmet for temporary storage because the mouthguard hangs down from the helmet when it is not used. However, while solving one problem, this strap design presents a possibly even greater problem. During the violent collisions which occur when football is played, a player's helmet is sometimes knocked off. If the player is using the mouthguard and the helmet is knocked off the player's head, the player's teeth can be severely damaged or knocked out depending upon the force exerted on the mouthguard from the impact to the helmet. Straps and tethers also present other problems for athletes. Players prefer not to have a loose, dangling mouthguard tethered to their helmet as the loose movement of the mouthguard is annoying or uncomfortable. Players also find straps and tethers unfavorable as they can limit the range of motion for the athlete as they move their heads in different positions.

Accordingly, a need exists for a mouthguard that properly fits with the teeth and jaw of a user to provide protection to the mouth and teeth of the user while also reducing the likelihood of contamination or loss during periods of non-use.

SUMMARY

New mouthguards that properly fit with the teeth and jaw of a user that provide protection to the mouth and teeth of the user while also providing an attachment arm for attaching the mouthguard to equipment and/or clothing of a user in between use is provided. This attachment feature reduces the likelihood of contamination or loss during periods of non-use since the mouthguard will not be placed flat on a contaminated surface but instead be attached to equipment, i.e. face grid of a helmet, avoiding direct contact to the outer surface of the mouthguard.

In one embodiment of the mouthguard according to the present disclosure a mouthguard comprising an outer portion and an inner portion forming a channel within the outer portion of the mouthguard and an attachment arm configured to extend from the mouthguard so as to temporarily attach the mouthguard to the user. The attachment arm is configured to fit with a cavity formed in the mouthguard so that the attachment arm can be extended out of the cavity to temporarily attach the mouthguard to the user's equipment and the extension arm can be positioned back into the cavity for storage.

Another embodiment of the present disclosure provides for a mouthguard assembly including a generally curved mouthguard for insertion into a user's mouth having an outer portion and inner portion, a channel formed within the inner portion of the mouthguard, and an attachment means to temporarily attach the mouthguard assembly to clothing or apparatus of the user. The attachment means is housed within the channel. The user can extend the attachment means out of the channel to temporarily attach the mouthguard assembly to clothing or apparatus of the user for storage.

The present disclosure also provides for a mouthguard system comprising a mouthguard for insertion into a user's mouth having an outer portion and inner portion and a channel formed within the inner portion of the mouthguard. The mouthguard further comprises an attachment arm that is configured to temporarily attach the mouthguard assembly to clothing or apparatus of the user in between uses. The attachment arm housed within a cavity configured in the outer portion of the mouthguard. The mouthguard and cavity are configured so that the user can extend the attachment means out from the mouthguard to form a hook-type configuration which can be used to temporarily attach the mouthguard to clothing or equipment in between uses, i.e. between plays in football. The mouthguard is equipped with a hinge that is attached to the mouthguard at one point and the attachment arm at the other so as to allow the attachment arm to have a stored position and an extended position. The hinge is configured to allow the attachment arm to move away from the stored position to the extended position and back to the stored position by manipulation about the hinge. In various embodiments, the attachment means includes a hook. In some embodiments, the attachment means includes a clip.

The mouthguard can also include a flavoring agent that is incorporated as part of the mouthguard so as to provide a pleasant taste when used. The system also has a storage case configured to fit the mouthguard wherein additional flavoring agents can be placed in the case so as to come in contact with the mouthguard when stored to enhance the flavor of the mouthguard while being stored in the storage case.

In various embodiments, the inner portion of the mouthguard can include an antimicrobial material selected to at least reduce bacteria harmful to humans, a flavoring agent, a cavity reducing material and/or a teeth whitening agent. In some embodiments where the inner portion of the mouthguard includes a cavity reducing material, the cavity reducing material can include fluoride.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties that are sought by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a handle" includes one, two, three or more handles.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications and equivalents which may be included within the invention as defined by the appended claims.

Figure 1:
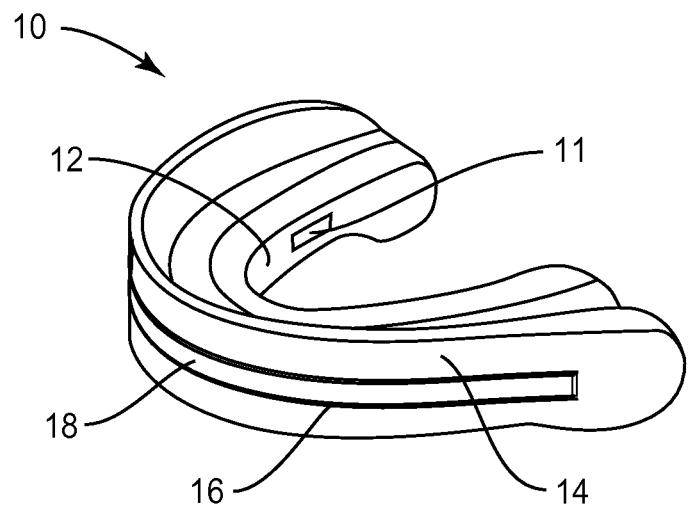
FIG. 1 is a perspective view of a mouthguard according to an exemplary embodiment of the present invention.
Figure 2:
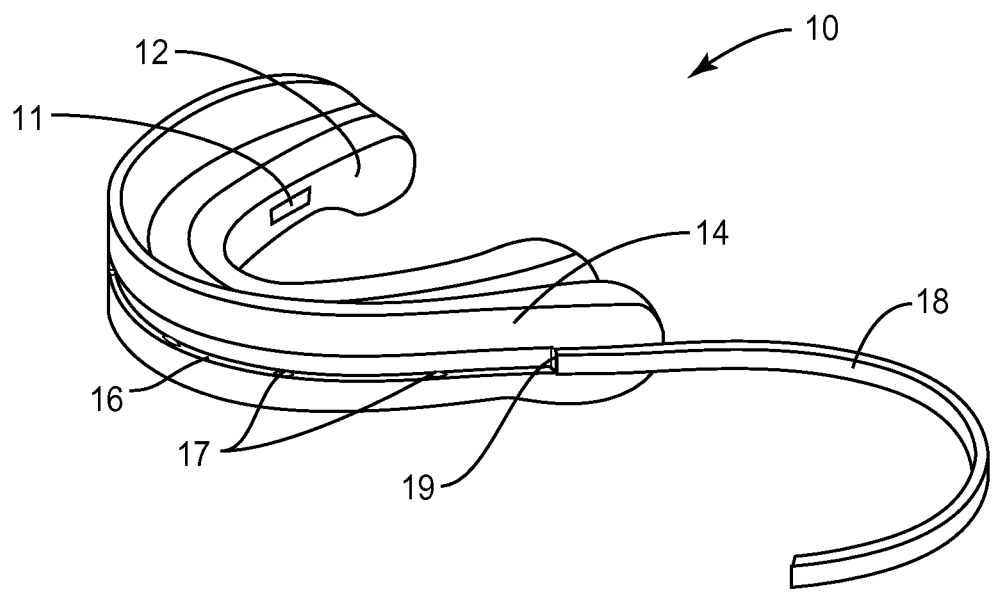
FIG. 2 is a perspective view of the mouthguard of FIG. 1 with an extension arm extended out of the channel formed within the outer portion of the mouthguard.

FIGS. 1 and 2 illustrate a perspective view of one embodiment of a mouthguard 10. As can be seen in FIG. 1, the mouthguard 10 has an inner portion 12 and an outer portion 14. The outer portion 14 includes a cavity 16 formed therein. The cavity 16 is configured to tightly fit an extension arm 18 which can be configured in the shape of hook so as to contour the front and side portions of mouthguard 10. The cavity can have protrusions 17 (FIG. 2) therein that are configured to secure the extension arm 18 in place once it is pushed into the cavity 16. The protrusions can be part of the molded mouthguard 10 and are malleable so that the extension arm 18 can be pulled over the protrusions so as to be released from the cavity 16. In an alternative embodiment of the mouthguard 10, a flexible strap can be fitted over the extension arm 18 when positioned within the cavity so as to prevent the extension arm from dislodging from the cavity 16 during use. The strap can be made from the same material as the mouthguard and can be fully attached to the mouthguard such that it can be slid out of the way so that the extension arm can be positioned into the cavity 16. Once in the cavity 16, the strap goes back to its original configuration holding the attachment arm in place.

In one embodiment of the mouthguard, the extension arm 18 and cavity 16 are configured so as to fit together in a compression fit arrangement. The cavity 16 and extension arm 18 extending from one side of the mouthguard 10, across the front of the mouthguard 10 to at least a portion of the opposite side of the mouthguard. This t hook configuration allows for easy attachment to equipment when the extension arm is extended out of the cavity and also provides a spring-like nature to the extension arm 18 that aids in keeping the extension arm 19 in place when stored in the cavity 16. This configuration is shown in FIG. 2.

Also shown in FIG. 1, at least one flavor pocket 11 is formed in the inner wall 12 of the mouthguard 10. The flavor pocket 11 is sized and shaped so as to accommodate a flavor containing capsule (not shown). The flavor containing capsule contains either a gel or fluid within and has a thin skin so that it easily bursts upon pressure being placed thereupon. Once the flavor capsule is inserted into the mouth guard and the mouth guard is in place, applying pressure either through the use of the tongue or by biting down flavor is released. The flavor can enter the oral cavity of the user through one or more flavor passages or in the alternative can leach from the material of the mouthguard 10 itself once the flavor capsule is ruptured.

That is, the flavor passages can be as simple as an opening in the inner wall 12 of the mouthguard 10 or can include accurate channels that extend between the flavor pocket and the inner surface of the inner wall so as to allow the flavor to flow from the flavor pocket to the oral cavity once the flavor capsule is ruptured.

The flavor passages can be slightly accurate or arched so as to form a vertical incline which will regulate the flow of gel flowing from the flavor capsule contained in the flavor pocket 11 through the arched channels and into the mouth of the user. Having this incline the user is able to take advantage of the flavor through an extended period of time over the course of a game and/or practice, rather than having the flavor from the capsules flow into his mouth quite readily and the taste be experienced only for a short time.

The flavor pocket may be fitted with an upper opening or slit in the rubberized material of the mouth guard which makes up the mouthpiece. The slit may be a flexible slit and would allow the user to slide the flavor gel capsule through the slit and into the flavor pocket. Once in place, the slit would then return back to its closed position, and therefore, would prevent the capsule from sliding out of the pocket inadvertently. This is important so as to prevent a choking hazard should the flavor capsule become dislodged due to blunt trauma.

FIG. 2 shows the extension arm 18 extending out of the cavity 16. As can be seen from the partial u-shaped configuration of the extension arm 18 it starts at one side of the mouthguard, across the front portion of the mouthguard 10 to the opposite side of the mouthguard 10. The extension arm 18 is attached to the mouthguard 10 by hinge 19 which allows the extension arm 18 to pivot from being positioned within cavity 16 to the extended position where it can be attached to equipment in between uses. In other embodiments, the extension arm can be attached within the cavity 16 by other known mechanisms similar to the hinge 19, including but not limited to, an arbor, axle, pivot, pole, shaft, spindle, stalk, stem, support, articulating point, turning point, junction, joint, and a union continuous with the material of the mouthguard.

Figure 3:
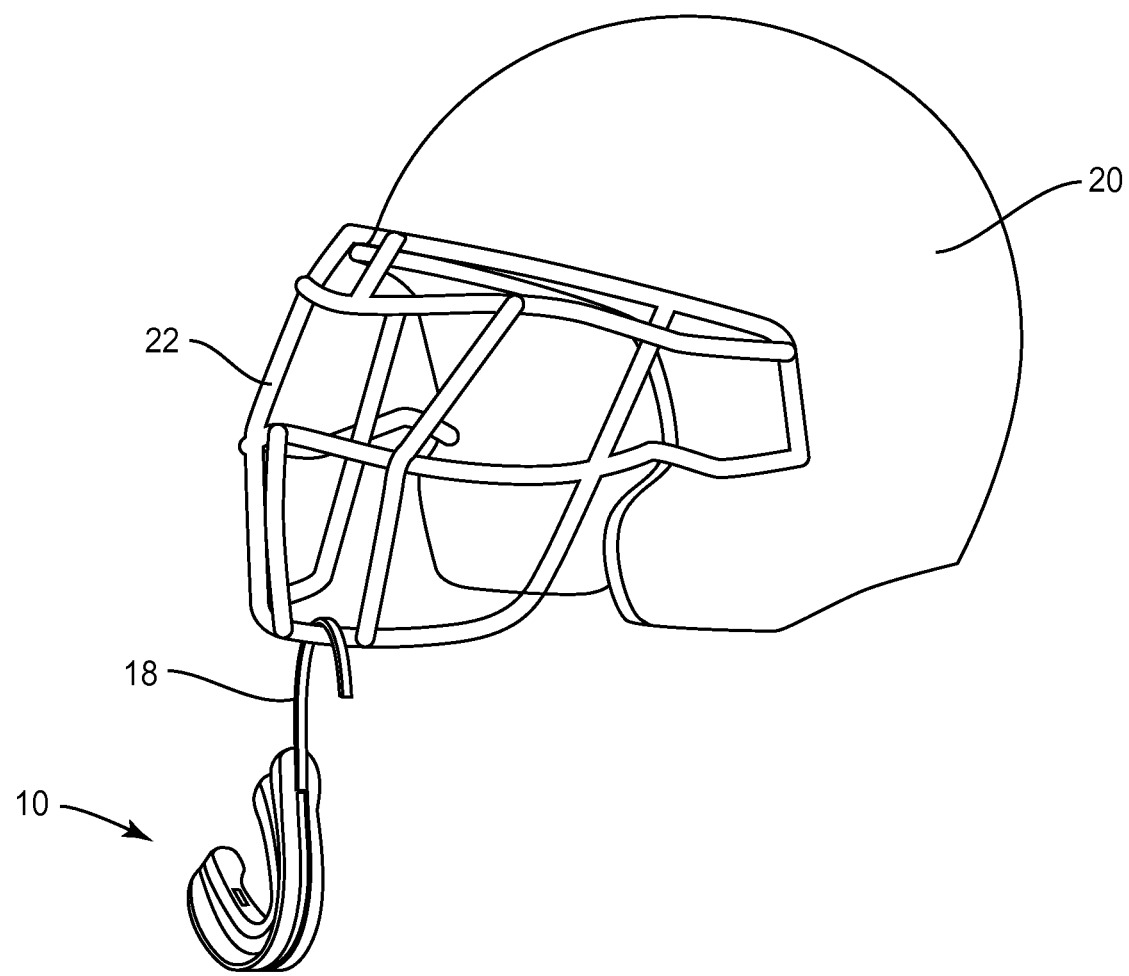
FIG. 3 is a perspective view of a football helmet with the mouthguard of FIG. 1 temporarily attached to the face mask of the helmet.
Figure 4:
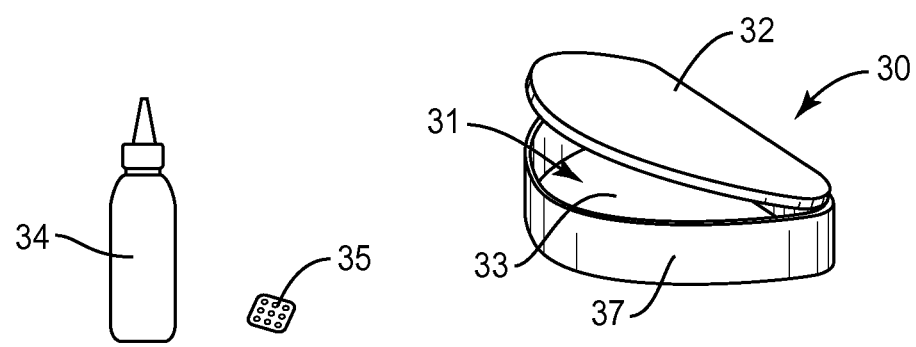
FIG. 4 is a perspective view of a case and flavoring for long-term storage of the mouthguard according to an exemplary embodiment of the present invention.

FIG. 3 shows the mouthguard 10 of FIGS. 1 and 2 in a temporary storage position on a football helmet 20. In particular, the extension arm 18 of the mouthguard 10 is extended out of the cavity 16 (not shown) and hooked onto the face mask 22 of the football helmet 20 between uses. The extension arm 18 can also be attached onto other areas of the face mask 22 or apparatus of the football player.

FIG. 3 shows a case 30 having a cavity 31 formed by the side walls 37 of the case which is configured to fit the mouthguard 10 of the present disclosure for storage of the mouthguard between games/practices. The case 30 having a lid 32 that can be partially attached at a joint so that it can be opened and closed to reveal the cavity 31 of the case. Cavity 31 configured to hold liquid or powdered flavoring agents. In the alternative, flavoring crystals and/or flavoring emulsion can be added to the cavity 31 and then water added do as to produce a flavoring solution that the mouthguard 10 can be stored. As the mouthguard remains in the flavored solution, the flavoring leaches into the mouthguard so that the mouthguard is re-charged with flavor for next use. In one embodiment of the present disclosure, the case material is coated or infused with an antibacterial agent such as, silver ions, so as to prevent bacterial growth in the case. In an alternative, additional bacterial agents can be added to the flavoring solution so as to prevent bacterial growth on the mouthguard itself during uses.

The size and/or dimensions of the mouthguard 10 in FIGS. 1-4 is such as to accommodate a variety of different individuals having different jaw sizes or jaw or tooth configurations. The mouthguard can be configured to protect the upper teeth, lower teeth or both in a bite-wing configuration.

The composition of the mouthguards in various embodiments includes one or more of EVA, polyurethane, polystyrene, polypropylene, high-density polyethylene, polycaprolactone and rubber. EVA that can be used includes but is not limited to materials such as DuPont Elvax No. 250 or Union Carbide DQDA No. 3269. Polypropylene if used exhibits a rigid character in that it holds its shape and polypropylene that can be used includes but is not limited to a material such as AP6112-HS from Huntsman Corporation, Chesapeake, Va. 23320. In one embodiment, the mouthguard includes a mixture of styrene block copolymer and high-density polyethylene. The styrene block copolymer may be DYNAFLEX® (part number 62780-0001) from GLS Corporation, 833 Ridgeview Drive, McHenry, Ill. 60050. In another embodiment, the mouthguard includes a mixture of styrene block copolymer and polyolefin elastomer, which is a copolymer of ethylene and octene-1. One copolymer that can be used as the polyolefin elastomer is available as ENGAGE® from Dupont Canada, Inc., P.O. Box 2200, Streetsville, Mississauga, Ontario L5M 2H3.

The composition of the attachment means in various embodiments includes one or more of ethyl vinyl acetate, polyurethane, polystyrene, polypropylene, high-density polyethylene, polycaprolactone and rubber. In some embodiments, the composition of the attachment means includes materials such that it is somewhat stiff and relatively inflexible so that it will remain largely in line and not twist or be overly flexible. In various embodiments where a hinge is used with the attachment means in the channel, the composition of the hinge includes one or more of ethyl vinyl acetate (EVA), polyurethane, polystyrene, polypropylene, high-density polyethylene, polycaprolactone and rubber.

The mouthguard 10 can also be made, in part, from thermal activated materials that soften when heated so as to receive an imprint of the teeth of a user and retain the imprint when cooled. This would aid in making a custom fit mouthguard for a user by placing the mouthguard 10 in warm water so as to soften the thermal activated material, pressing against the user's teeth and holding it in place until the mold is cooled and the imprint is retained. In alternative embodiment, the mouthguard can also include a plurality of protrusions which aid in closely fitting the mouthguard to the teeth of the user.

As discussed above, in various embodiments, the inner portion of the mouthguard can include an antimicrobial material selected to at least protect users from harmful bacteria or other organisms. The antimicrobial material can be non-toxic and free of heavy metal for resisting the growth of microbials. In some embodiments, the antimicrobial material can be one or more of chlorinated phenol (e.g. 5-chloro-2-(2,-4-dichlorophenoxy)phenol); polyhexamethylene biguanide hydrochloride; doxycycline; chlorhexidine; metronidazole; thymol; eucalypol; methyl salycilate; water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters and halogenated carbanilides; water soluble antimicrobials such as quaternary ammonium salts and bis-biquamide salts; and triclosan monophosphate.

Also as discussed above, in various embodiments, the inner portion of the mouthguard can include one or more of a flavoring agent, a sweetening agent, a cooling agent, a salivating agent, a warming agent and a numbing agent. The flavoring agent can be one or more of a wide variety of materials including but not limited to oil of wintergreen, oil of peppermint, oil of spearmint, clove bud oil, menthol, anethole, methyl salicylate, eucalyptol, *cassia,* 1-menthyl acetate, sage, eugenol, parsley oil, oxanone, alpha-irisone, marjoram, lemon, orange, propenyl guaethol, cinnamon, vanillin, thymol, linalool, and cinnamaldehyde glycerol acetal known as CGA. The sweetening agent can be one or more of sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin.

The cooling agent in various embodiments can be one or more of a wide variety of materials including but not limited to carboxamides, menthol, ketals and diols. In some embodiments, the cooling agent can be a paramenthan carboxyamide agent such as N-ethyl-p-menthan-3-carboxamide (known commercially as "WS-3"), N,2,3-trimethyl-2-isopropylbutanamide (known as "WS-23") and mixtures thereof. In some exemplary embodiments, the cooling agent is one or more of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms "menthol" and "menthyl" as used herein include dextro- and levorotatory isomers of these compounds and racemic mixtures thereof.

The salivating agent in various embodiments is known as Jambu® and is manufactured by Takasago. The warming agent in various embodiments can be capsicum and/or nicotinate esters such as benzyl nicotinate. The numbing agent in various embodiments can be one or more of benzocaine, lidocaine, clove bud oil and ethanol.

The flavoring agents can be in the form of an emulsion dispersed throughout the mouthguard 10, flavoring crystals embedded in the material of the mouthguard and topical flavoring on the mouthguard in the form of a solution, gel and/or powder. The amount of a flavoring agent, a sweetening agent, a cooling agent, a salivating agent, a warming agent and/or a numbing agent included in a mouthguard is an amount sufficient to provide a user with the desired effect for a reasonable usage period for the mouthguard. In some embodiments, the afore-mentioned agents are included in a crystal form where they are released as the mouthguard is used over a period of time.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A mouth guard apparatus comprising:
   a mouthpiece having an outer portion and an inner portion, said inner portion forming a channel for receiving the user's teeth;
   a cavity situated on said outer portion of said mouthpiece, wherein a length of said cavity is at least half of a length of said outer portion of said mouthpiece; and
   a rigid hook hingedly attached to a portion of said mouthpiece, said hook is situated on the same plane as said cavity, at least a portion of said hook is situated within said cavity during a stored position, said hook extends outwardly away from said cavity during a use position.

2. The apparatus of claim 1 wherein said mouthpiece comprises top and bottom portions.

3. The apparatus of claim 2 wherein said cavity is situated adjacent said bottom portion of said mouthpiece.

4. The apparatus of claim 1 wherein said hook is designed to be attached onto a user's article of clothing during said use position.

5. The apparatus of claim 1 wherein said hook is designed to be attached to a user during said use position.

6. The apparatus of claim 1 wherein said hook is configured to be compression fitted within said cavity during said stored position.

7. The apparatus of claim 1 wherein said mouthpiece is constructed of a material selected from the group comprising ethyl vinyl acetate, polyurethane, polystyrene, polypropylene, polyethylene, rubber, polycaprolactone and mixture thereof.

8. The apparatus of claim 1 further comprising an antibacterial agent.

9. The apparatus of claim 1 further comprising a flavoring agent.

10. A single mouth guard apparatus comprising:
    a mouthpiece having upper, lower, outer and inner portions, said inner portion forming a channel for receiving the user's teeth, said channel forming an opening on said upper portion of said mouthpiece;
    a cavity situated on said outer portion and adjacent to said lower portion of said mouthpiece, wherein a length of said cavity is at least half of a length of said outer portion of said mouthpiece; and
    a rigid hook pivotally attached to a portion of said mouthpiece and situated adjacent said cavity, said hook is situated on the same plane as said cavity, at least a portion of said hook is situated within said cavity during a stored position, said hook extends outwardly away from said cavity during a use position.

11. The apparatus of claim 10 wherein said hook is designed to be attached onto a user's article of clothing during said use position.

12. The apparatus of claim 10 wherein said hook is designed to be attached to a user during said use position.

13. The apparatus of claim 10 wherein said hook is configured to be compression fitted within said cavity during said stored position.

14. The apparatus of claim 10 further comprising an antibacterial agent.

15. The apparatus of claim 10 further comprising a flavoring agent.

16. A double mouth guard apparatus comprising:
    a mouthpiece having upper, lower, outer and inner portions, said inner portion forming at least two channels for receiving the upper and lower teeth of a user, said channels forming an opening on said upper and said lower portions of said mouthpiece;
    a cavity situated on said outer portion of said mouthpiece, wherein a length of said cavity is at least half of a length of said outer portion of said mouthpiece; and
    a rigid attachment arm pivotally attached to a portion of said mouthpiece and situated adjacent said cavity, said attachment arm is situated on the same plane as said cavity, at least a portion of said attachment arm is situated within said cavity during a stored position, said attachment arm extends outwardly away from said cavity during a use position, said attachment arm is selected from a group comprising hooks, clips and combination thereof.

17. The apparatus of claim 16 wherein said attachment arm is configured to be compression fitted within said cavity during said stored position.

18. The apparatus of claim 16 further comprising an antibacterial agent.

19. The apparatus of claim 16 further comprising a flavoring agent.

* * * * *